(12) United States Patent
Ridley, Jr. et al.

(10) Patent No.: US 11,845,713 B2
(45) Date of Patent: Dec. 19, 2023

(54) BIOGAS CONVERSION TO MIXED ALCOHOLS

(71) Applicant: Standard Alcohol Company of America, Inc., Denver, CO (US)

(72) Inventors: Richard Denham Ridley, Jr., Berthoud, CO (US); Michael Emory Pardun, Denver, CO (US)

(73) Assignee: Standard Alcohol Company of America, Inc., Denver, CO (US)

( * ) Notice: Subject to any disclaimer, the term of this patent is extended or adjusted under 35 U.S.C. 154(b) by 62 days.

(21) Appl. No.: 17/578,389

(22) Filed: Jan. 18, 2022

(65) Prior Publication Data

US 2022/0234975 A1 Jul. 28, 2022

Related U.S. Application Data

(60) Provisional application No. 63/140,282, filed on Jan. 22, 2021.

(51) Int. Cl.
*C07C 29/151* (2006.01)
*C07C 29/48* (2006.01)
(Continued)

(52) U.S. Cl.
CPC ............ *C07C 29/48* (2013.01); *C01B 3/34* (2013.01); *C01B 3/52* (2013.01); *C07C 29/153* (2013.01);
(Continued)

(58) Field of Classification Search
None
See application file for complete search history.

(56) References Cited

U.S. PATENT DOCUMENTS

2007/0010588 A1  1/2007  Pearson
2007/0155999 A1*  7/2007  Pujado .............. C07C 29/151
                                          422/600
(Continued)

OTHER PUBLICATIONS

EPA456-R-20-001, published Jul. 2020, pp. 1-55 (Year: 2020).*
(Continued)

*Primary Examiner* — Medhanit W Bahta
(74) *Attorney, Agent, or Firm* — O'Connor & Company; Ryan P. O'Connor (57) ABSTRACT

Some variations provide a process for producing mixed alcohols, comprising: purifying a biogas feedstock to generate a renewable natural gas stream comprising methane; introducing the renewable natural gas stream into a methane-to-syngas unit operated at effective conditions to convert the methane to a first syngas stream containing at least $H_2$, CO, and $CO_2$; purifying the first syngas stream, including separating the $CO_2$ from the first syngas stream, and optionally separating some of the $H_2$ from the first syngas stream, thereby generating a clean syngas stream; introducing the clean syngas stream into a mixed-alcohol reactor operated at effective alcohol synthesis conditions with an alcohol-synthesis catalyst, thereby generating mixed alcohols; and purifying the mixed alcohols to generate a mixed-alcohol product. The mixed-alcohol product may be blended with a hydrocarbon fuel, such as gasoline, to produce a blended fuel. The blended fuel has significantly lower carbon intensity than the base hydrocarbon fuel.

18 Claims, 2 Drawing Sheets

(51) Int. Cl.
*C01B 3/34* (2006.01)
*C01B 3/52* (2006.01)
*C07C 29/74* (2006.01)
*C10L 1/04* (2006.01)
*C07C 29/153* (2006.01)

(52) U.S. Cl.
CPC ............... *C07C 29/74* (2013.01); *C10L 1/04* (2013.01); *C01B 2203/0475* (2013.01); *C01B 2203/061* (2013.01); *C01B 2203/1241* (2013.01); *C01B 2203/1258* (2013.01)

(56) References Cited

U.S. PATENT DOCUMENTS

| | | | |
|---|---|---|---|
| 2008/0220489 A1* | 9/2008 | Offerman | C10L 1/023 435/157 |
| 2011/0175032 A1* | 7/2011 | Gunther | C01B 3/382 252/373 |
| 2012/0267577 A1 | 10/2012 | Sceats et al. | |
| 2020/0148964 A1 | 5/2020 | Foody et al. | |
| 2022/0119715 A1* | 4/2022 | Greager | C10G 2/30 |

OTHER PUBLICATIONS

Dobladez, J. A. D. et al. "Efficient recovery of syngas from dry methane reforming product by a dual pressure swing adsorption process" International J. Hydrogen Energy 46 (2021) 17522-17533; Available online Mar. 18, 2020 (Year: 2020).*

PCT/US2022/012843, International Search Report and Written Opinion by ISA/US, dated Apr. 8, 2022.

* cited by examiner

BIOGAS CONVERSION TO MIXED ALCOHOLS

PRIORITY DATA

This patent application claims priority to U.S. Provisional Patent Application No. 63/140,282 filed on Jan. 22, 2021, which is hereby incorporated by reference herein.

FIELD OF THE INVENTION

The present invention generally relates to processes and systems for producing mixed alcohols from biogas, and for producing fuels with low carbon intensity.

BACKGROUND OF THE INVENTION

Currently, syngas is produced in the United States primarily through steam methane reforming (SMR) technology, and primarily from fossil natural gas found in natural gas fields, oil well fields, or coal beds. The produced syngas is then used for production of chemicals, fuel additives, or fertilizers. The produced syngas may also be water-gas shifted for increased hydrogen production, with that hydrogen often being used in the production of high-carbon-intensity gasoline.

Steam reforming of natural gas is the largest global source of hydrogen. The production of hydrogen is very important industrially, since hydrogen is required for many essential chemical processes. Hydrogen is used in the industrial synthesis of ammonia via the Haber process, for example. Other uses of hydrogen include oil refining (e.g., hydrotreating or hydrodesulfurization), methanol production, transportation fuels, and hydrogen fuel cells, to name a few.

Conventional steam methane reforming mixes natural gas and steam and uses an external source of hot gas to heat SMR tubes in which an endothermic catalytic reaction takes place. The steam reacts directly with methane, commonly using a nickel-based catalyst, to produce a gas stream of carbon monoxide (CO), hydrogen ($H_2$), carbon dioxide ($CO_2$), and small amounts of unconverted methane ($CH_4$) as well as any nitrogen ($N_2$) that entered with the feed gas. The produced gas stream is referred to as synthesis gas or syngas.

Other methane-to-syngas conversion processes utilize autothermal reforming or partial oxidation. In partial oxidation (PDX), a catalyst is utilized to partially oxidize methane with oxygen (pure or in air) to generate syngas. Because it is exothermic, catalytic partial oxidation is less energy-intensive than endothermic steam-methane reforming. Autothermal reforming (ATR) uses oxygen and carbon dioxide or steam in a reaction with methane to form syngas. The reaction usually takes place in a single chamber where the methane is partially oxidized in an exothermic process. The main difference between autothermal reforming and steam-methane reforming is that steam-methane reforming does not require oxygen. Autothermal reforming can be regarded as a hybrid of steam-methane reforming and partial oxidation, in which $H_2/CO$ ratios can be readily varied by adjusting the $H_2O$ and $CO_2$ concentrations in the feed gas. Methane dry reforming is an alternative process for producing syngas by reacting $CH_4$ with $CO_2$ in a highly endothermic catalyzed reaction at high temperatures. This process is not widely used in the gas-processing industries because of rapid catalyst deactivation due to carbon deposition.

The following reactions take place in steam reforming of methane:

$CH_4 + H_2O$ (steam) → $CO + 3H_2$ (Endothermic)

$CO + H_2O$ (steam) → $CO_2 + H_2$ (Exothermic)

where the first reaction is the primary reaction of methane with water to form one molecule of CO and three molecules of $H_2$, and the second reaction is the water-gas shift reaction that converts a molecule of CO (from the primary reaction) into $CO_2$ by removing an oxygen atom from water to make more hydrogen. In industrial practice, there may be a separate water-gas shift reactor downstream of the steam methane reformer.

One commercial use of purified syngas is the production of mixed alcohols, such as a mixture of $C_1$-$C_5$ alcohols. Mixed alcohols have excellent fuel characteristics for vehicle engines, including high oxygenate content, good octane value, and lower vapor pressure than ethanol alone. Mixed alcohols may be synthesized by passing cleaned syngas over a potassium-promoted CoS—$MoS_2$ catalyst. See U.S. Pat. Nos. 4,752,622 and 4,882,360, which are hereby incorporated by reference. Processes and catalysts for making mixed alcohols are also described in U.S. Pat. Nos. 8,921,431 and 9,290,425, which are hereby incorporated by reference. The mixed alcohol may be blended with gasoline.

Improved hydrocarbon fuel compositions, and processes to make them, are desired—especially with an aim to reduce the carbon intensity of the hydrocarbon fuel (e.g., gasoline). In particular, what is sought is a blended fuel that has significantly lower carbon intensity than a starting hydrocarbon fuel.

SUMMARY OF THE INVENTION

The present invention addresses the aforementioned needs in the art.

Some variations provide a process for producing mixed alcohols, the process comprising:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream;

(e) introducing the clean syngas stream into a mixed-alcohol reactor operated at effective alcohol synthesis conditions and in the presence of an alcohol-synthesis catalyst, thereby generating mixed alcohols and a reactor off-gas; and (f) optionally purifying the mixed alcohols to generate a mixed-alcohol product.

In some embodiments, the biogas feedstock is obtained from a source selected from the group consisting of a landfill, an industrial compost facility, an anaerobic digestor, and combinations thereof. In certain embodiments, the anaerobic digestor is configured for anaerobic digestion of animal waste.

In some embodiments, step (b) utilizes water scrubbing, chemical scrubbing, or a combination thereof to remove at least some carbon dioxide from the biogas feedstock. In these or other embodiments, step (b) may utilize a membrane to remove at least some carbon dioxide from the biogas feedstock.

In some embodiments in which the biogas feedstock contains $H_2S$, step (b) may utilize absorption of the $H_2S$ into an absorption media to remove at least some of the $H_2S$ from the biogas feedstock.

In some embodiments, step (b) utilizes drying to remove at least some water from the biogas feedstock.

The methane-to-syngas unit may be selected from the group consisting of a steam reforming reactor, an autothermal reforming reactor, a partial-oxidation reactor, and combinations thereof.

In some embodiments, in step (c), a pipeline natural gas stream is co-fed, along with the renewable natural gas stream, to the methane-to-syngas unit.

In some embodiments, in step (d), at least some of the $H_2$ is separated and recovered from the first syngas stream. At least some of this $H_2$ may be used as fuel within the process. Alternatively, or additionally, at least some of the $H_2$ is recovered as a motor fuel. Alternatively, or additionally, at least some of the $H_2$ is recovered and utilized in an oil and gas refinery.

In some embodiments, step (d) utilizes an amine-based system, a cryogenic system, a membrane-separation system, a pressure-swing adsorption unit, or a combination thereof.

In some embodiments, the $CO_2$ separated in step (d) is recovered and sequestered in a geological formation. Alternatively, or additionally, the $CO_2$ separated in step (d) may be recovered and utilized in enhanced oil recovery.

In some embodiments, in step (d), nitrogen is separated from the first syngas stream. The nitrogen may be purged from the process and released to the atmosphere or recovered for other uses, such as production of a liquid nitrogen co-product.

In some embodiments, in step (d), a methane-rich stream is separated from the first syngas stream. The methane-rich stream may be recycled to the methane-to-syngas unit. Alternatively, or additionally, the methane-rich stream may be combusted to provide heat to the methane-to-syngas unit.

In some preferred embodiments, in step (e), the alcohol-synthesis catalyst is a metal sulfide catalyst.

In some embodiments, step (f) is conducted and includes one or more of sulfur removal, dehydration, and distillation.

The reactor off-gas may be recycled to step (d). Optionally, the reactor off-gas is treated in a $H_2S$ removal unit prior to recycling to step (d).

In some embodiments, step (f) is conducted to produce a mixed-alcohol product. The mixed-alcohol product may be blended with a hydrocarbon fuel selected from gasoline, diesel fuel, or jet fuel, to produce a blended fuel. In some embodiments, the blended fuel has at least 10% lower carbon intensity than the hydrocarbon fuel. In preferred embodiments, the blended fuel has at least 20% lower carbon intensity than the hydrocarbon fuel. In even more-preferred embodiments, the blended fuel has at least 30% lower carbon intensity than the hydrocarbon fuel.

Other variations provide a process for producing mixed alcohols, the process comprising:

(a) obtaining a biogas feedstock;

(b) purifying the biogas feedstock to generate a renewable natural gas stream comprising methane;

(c) introducing the renewable natural gas stream to a pipeline, wherein the renewable natural gas stream is co-mingled with other natural gas contained within the pipeline;

(d) withdrawing a stream of natural gas from the pipeline;

(e) introducing the stream of natural gas into a methane-to-syngas unit operated at effective conditions to convert the methane to a first syngas stream containing at least $H_2$, CO, and $CO_2$;

(f) purifying the first syngas stream, including separating the $CO_2$ from the first syngas stream, and optionally separating some of the $H_2$ from the first syngas stream, thereby generating a clean syngas stream;

(g) introducing the clean syngas stream into a mixed-alcohol reactor operated at effective alcohol synthesis conditions and in the presence of an alcohol-synthesis catalyst, thereby generating mixed alcohols and a reactor off-gas; and (h) optionally purifying the mixed alcohols to generate a mixed-alcohol product.

In some embodiments, step (c) generates a renewable natural gas credit that applies to the mixed alcohols produced in step (g).

When step (h) is conducted, step (c) may generate a renewable natural gas credit that applies to the mixed-alcohol product produced in step (h).

The biogas feedstock may be obtained from a source selected from the group consisting of a landfill, an industrial compost facility, an anaerobic digestor, and combinations thereof. An anaerobic digestor may be configured for anaerobic digestion of animal waste, for example.

Step (b) may utilize water scrubbing, chemical scrubbing, or a combination thereof to remove at least some carbon dioxide from the biogas feedstock. In some embodiments, step (b) utilizes a membrane to remove at least some carbon dioxide from the biogas feedstock.

When the biogas feedstock contains $H_2S$, step (b) may utilize absorption of the $H_2S$ into an absorption media to remove at least some of the $H_2S$ from the biogas feedstock.

In some embodiments, step (b) utilizes drying to remove at least some water from the biogas feedstock.

The methane-to-syngas unit may be selected from the group consisting of a steam reforming reactor, an autothermal reforming reactor, a partial-oxidation reactor, and combinations thereof.

In some processes, in step (e), a pipeline natural gas stream is co-fed, along with the renewable natural gas stream (withdrawn in step (d)), to the methane-to-syngas unit. Typically, the pipeline natural gas stream is distinct from the initial natural gas that is co-mingled with the renewable natural gas stream in step (c).

In some embodiments, in step (f), at least some of the $H_2$ is separated and recovered from the first syngas stream. At least some of this $H_2$ may be used as fuel within the process. Alternatively, or additionally, at least some of the $H_2$ is recovered as a motor fuel. Alternatively, or additionally, at least some of the $H_2$ is recovered and utilized in an oil and gas refinery.

In some embodiments, step (f) utilizes an amine-based system, a cryogenic system, a membrane-separation system, a pressure-swing adsorption unit, or a combination thereof.

In some embodiments, the $CO_2$ separated in step (f) is recovered and sequestered in a geological formation. Alternatively, or additionally, the $CO_2$ separated in step (f) may be recovered and utilized in enhanced oil recovery.

In some embodiments, in step (f), nitrogen is separated from the first syngas stream. The nitrogen may be purged from the process and released to the atmosphere or recovered for other uses, such as production of a liquid nitrogen co-product.

In some embodiments, in step (f), a methane-rich stream is separated from the first syngas stream. The methane-rich stream may be recycled to the methane-to-syngas unit. Alternatively, or additionally, the methane-rich stream may be combusted to provide heat to the methane-to-syngas unit.

In some preferred embodiments, in step (g), the alcohol-synthesis catalyst is a metal sulfide catalyst.

In some embodiments, step (h) is conducted and includes one or more of sulfur removal, dehydration, and distillation.

The reactor off-gas may be recycled to step (f). Optionally, the reactor off-gas is treated in a $H_2S$ removal unit prior to recycling to step (f).

In some embodiments, step (h) is conducted to produce a mixed-alcohol product. The mixed-alcohol product may be blended with a hydrocarbon fuel selected from gasoline, diesel fuel, or jet fuel, to produce a blended fuel. In some embodiments, the blended fuel has at least 10% lower carbon intensity than the hydrocarbon fuel. In preferred embodiments, the blended fuel has at least 20% lower carbon intensity than the hydrocarbon fuel. In even more-preferred embodiments, the blended fuel has at least 30% lower carbon intensity than the hydrocarbon fuel.

Some variations of the invention provide a system configured to carry out a disclosed process. Other variations provide a mixed-alcohol composition produced by a disclosed process.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

For purposes of an enabling technical disclosure, various explanations, hypotheses, theories, speculations, assumptions, and so on are disclosed. The present invention does not rely on any of these being in fact true. None of the explanations, hypotheses, theories, speculations, or assumptions in this detailed description shall be construed to limit the scope of the invention in any way.

The present inventors have discovered, among other things, that renewable natural gas derived from biogas enables a syngas producer to control the carbon intensity of the syngas, which in turn significantly impacts the carbon intensity of the final product made from that syngas. In particular, variations of the present invention are predicated on an integrated process to convert biogas (such as animal waste gas or landfill gas) to produce a mixed-alcohol product. This may be accomplished, for example, by first cleaning up the biogas to produce renewable natural gas (RNG) and then using that RNG as a partial or complete feedstock to a syngas generator (e.g., SMR, ATR, or PDX units). The use of RNG significantly lowers the carbon intensity (CI) of the produced syngas, for multiple reasons including the avoidance of methane that would otherwise be emitted to the atmosphere (methane is a potent greenhouse gas). When mixed alcohols are produced from the syngas, the carbon intensity of the mixed-alcohol product can be very low or even negative.

In some variations, biogas is produced from landfill recovery or anaerobic digestion of animal waste. Biogas typically contains 55-65 vol % methane, 30-45 vol % $CO_2$, and 0.1-3 vol % $H_2S$. Due to the high $CO_2$ content, the presence of $H_2S$, and the low BTU (energy) value, the biogas is preferably upgraded to typical pipeline specifications of natural gas. Upgrading of the biogas may be accomplished by water or chemical scrubbing or the use of specialty membranes to remove the $CO_2$, and then absorption of the $H_2S$, followed by drying of the gas to remove retained water. Once the biogas has been upgraded to pipeline specifications, the biogas is considered to be "renewable natural gas" (RNG).

The RNG may be fed to a syngas generator directly. Alternatively, or additionally, the RNG may be transferred to a commercial natural gas pipeline system where it is co-mingled with fossil natural gas. A user then removes gas from the pipeline just as the user does fossil natural gas and uses the pipeline gas as a feed to a syngas generator. The syngas generator produces a mixture of hydrogen ($H_2$), carbon monoxide (CO), and carbon dioxide ($CO_2$), with small amounts of methane ($CH_4$) and nitrogen ($N_2$). This syngas mixture is preferably processed through a gas separation system—typically an amine system or membranes—to remove $CO_2$, $CH_4$, and $N_2$ as well as any excess $H_2$. The recovered $CO_2$ may be used for enhanced oil recovery or sequestration. The excess $H_2$ is sent to either fuel or sales, and the nitrogen is vented to atmosphere.

The remaining cleaned syngas ($H_2$ and CO) is then further compressed and sent to a mixed-alcohol reactor unit, in which the CO and $H_2$ are heated and passed over a catalyst so that a portion of the syngas is converted to mixed alcohols. The unreacted syngas, along with small quantities of $CO_2$ and $CH_4$, are blended back into the fresh syngas for separation along with the gas from the syngas generator.

Some variations provide a process for producing mixed alcohols, the process comprising:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream;

(e) introducing the clean syngas stream into a mixed-alcohol reactor operated at effective alcohol synthesis conditions and in the presence of an alcohol-synthesis catalyst, thereby generating mixed alcohols and a reactor off-gas; and (f) optionally purifying the mixed alcohols to generate a mixed-alcohol product.

Figure 1:
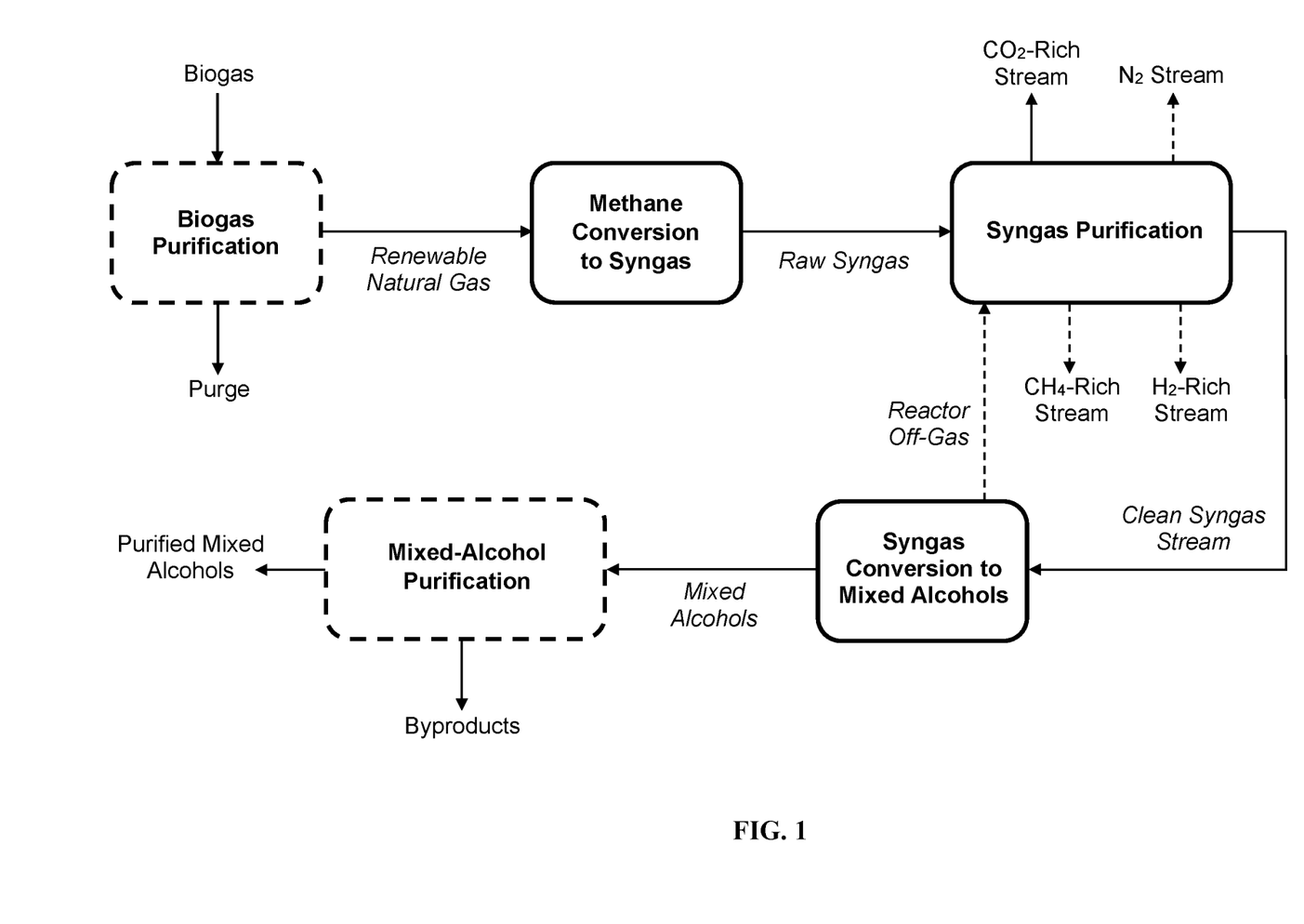
FIG. 1 is an exemplary block-flow diagram according to some embodiments for mixed-alcohol production from biogas.

FIG. 1 is an exemplary block-flow diagram according to some embodiments for mixed-alcohol production from biogas. Note that not all process boxes in FIG. 1 are required in all embodiments. Dotted boxes and lines denote optional units and streams, respectively.

In some embodiments, the biogas feedstock is obtained from a source selected from the group consisting of a landfill, an industrial compost facility, an anaerobic digestor, and combinations thereof. In certain embodiments, the anaerobic digestor is configured for anaerobic digestion of animal waste.

The composition of the biogas feedstock usually varies from different sources. As one example, landfill gas often has somewhat higher $CO_2$ content and somewhat lower $CH_4$ content compared to animal gas. The processes disclosed herein may be adjusted to account for the composition of the starting biogas feedstock.

Various biogas sources will be further described, without limiting the scope of the present invention.

Generally speaking, biogas may be recovered from an anaerobic digestor that digests biodegradable material, a landfill, an industrial compost facility, a wastewater treatment plant, or a biorefinery that co-produces biogas from biomass.

Landfill gas (LFG) is a natural byproduct of the decomposition of organic material in landfills. Instead of escaping into the air, LFG can be captured, converted, and used as a renewable energy resource. LFG may be collected through vertical and horizontal piping buried in a landfill. Using LFG helps to reduce odors and other hazards associated with LFG emissions, and prevents methane from migrating into the atmosphere.

Municipal solid waste (MSW) landfills are the third-largest source of human-related methane emissions in the United States. At the same time, methane emissions from MSW landfills represent a lost opportunity to capture and use a significant energy resource.

When MSW is first deposited in a landfill, it undergoes an aerobic (with oxygen) decomposition stage when little methane is generated. Then, typically within less than 1 year, anaerobic conditions are established and methane-producing bacteria begin to decompose the waste and generate methane. Bacteria usually decompose landfill waste in four phases. Gas composition changes with each phase, and waste in a landfill may be undergoing several phases of decomposition at once. The methane content may therefore vary depending on the decomposition phase when the LFG is collected. LFG may be extracted from landfills using a series of wells and a blower/flare (or vacuum) system. This system directs the collected gas to a central point where it can be processed and upgraded to RNG as disclosed herein.

When biogas used herein is recovered from an anaerobic digestor, anaerobic digestion is employed. Anaerobic digestion is a series of biological processes in which microorganisms break down biodegradable material in the absence of oxygen. One of the end products is biogas. Known anaerobic digestion technologies can convert livestock manure, municipal wastewater solids, food waste, industrial wastewater residuals, fats, oils, grease, and various other organic waste streams into biogas. Separated digested solids can be composted, utilized for animal bedding, directly applied to cropland, or converted into other products. Nutrients in the liquid stream may be used in agriculture as fertilizer.

The conventional digestion process begins with bacterial hydrolysis of the input materials in order to break down insoluble organic polymers such as carbohydrates and make them available for other bacteria. Acidogenic bacteria then convert the sugars and amino acids into carbon dioxide, hydrogen, ammonia, and organic acids. Acetogenic bacteria convert the organic acids into acetic acid, along with additional ammonia, hydrogen, and carbon dioxide. Finally, methanogens convert these products to methane and carbon dioxide.

Anaerobic digestion may convert a lignocellulosic feedstock to methane. A lignocellulosic feedstock contains at least cellulose and typically contains lignin. Anaerobic digestion can accommodate a wide range of feedstocks of various types, sizes, and moisture contents. For example, biomass such as agricultural wastes, forest products, grasses, and other cellulosic material may be used. In various embodiments, the lignocellulosic feedstock includes one or more materials selected from grass straw, corn stover, wheat straw, rice straw, cotton burr, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, timber harvesting residues, softwood chips, hardwood chips, tree branches, tree stumps, leaves, bark, sawdust, paper, cardboard, or off-spec paper pulp. A person of ordinary skill in the art will appreciate that the feedstock options are virtually unlimited. The feedstock may be milled using known apparatus, such as hammer mills, duplex mills, shredders, Valley beaters, disk refiners, conical refiners, or cylindrical refiners, for example.

Anaerobic digestion may utilize a waste feedstock, such as food waste, agricultural organic waste, industrial organic waste, livestock manure, or a combination thereof, for example. A waste feedstock may or may not contain cellulose and/or lignin. Cow manure, for example, contains cellulose and lignin that is not digested. Certain food wastes may contain high amounts of oils and/or starches but contain substantially no cellulose or lignin.

Anaerobic digesters can be designed and engineered to operate using a number of different configurations and can be categorized into batch vs. continuous process mode, mesophilic vs. thermophilic temperature conditions, high solids vs. low solids, and single stage vs. multistage processes.

In a batch system, feedstock is added to the reactor (anaerobic digester) at the start of the process. The reactor is then sealed for the duration of the process. In its simplest form, batch processing utilizes inoculation with already processed material to start the anaerobic digestion. In continuous digestion processes, organic matter is constantly added or is added at multiple times to the reactor. Examples of this form of anaerobic digestion include continuous stirred-tank reactors, upflow anaerobic sludge blankets, expanded granular sludge beds, and internal circulation reactors. Fed-batch anaerobic digestion is also possible, in which feedstock is continuously fed but product biogas is not removed until the end of the batch process. An anerobic digestor may also be designed and operated continuously.

Anaerobic digesters essentially carry out fermentation to ultimately produce $CH_4$ and $CO_2$. Fermentation conditions in the anaerobic digesters are conditions that generate at least some methane-containing biogas from the input material. The fermentation temperature may be selected from about 20° C. to about 70° C., for example. The fermentation temperatures for anaerobic digesters are preferably selected based on the species of methanogens (or other microorganisms) in the digesters. Mesophilic digestion takes place at temperatures from about 20° C. to about 45° C., when mesophilic microorganisms are present. Thermophilic digestion takes place from about 50° C. to about 70° C., when thermophilic microorganisms are present. Thermophilic temperatures enhance the disintegration and gas production from the feedstock. Microorganisms are typically bacteria but may be yeasts. Exemplary microorganisms include, but are not limited to, *Clostridium, Pseudomonas, Eubacterium, Mathenaosarcina, Methanosaeta*, and *Methanobacterium* species.

The fermentation residence time in an anaerobic digester varies with the amount and type of feed material and with the reactor configuration. The fermentation time may be selected from about 5 days to about 60 days, for example. In a typical two-stage mesophilic digestion, residence time varies between about 10 to 60 days, while for a single-stage thermophilic digestion, residence times is normally faster such as about 5 to 40 days. The fermentation pH may be selected from about 6.5 to about 8.5, for example.
This specification hereby incorporates by reference Taricska et al., "Anaerobic Digestion" In: *Biosolids Treatment Processes. Handbook of Environmental Engineering*, Vol 6. Humana Press, 2007 for its teachings of the design and operation of anaerobic digesters, in some embodiments.

Step (b) is preferably included in the process to purify the biogas, although the necessity of step (b) will depend on the source of the biogas and its quality. In some embodiments, step (b) utilizes water scrubbing, chemical scrubbing, or a combination thereof to remove at least some carbon dioxide from the biogas feedstock. In these or other embodiments, step (b) may utilize a membrane to remove at least some carbon dioxide from the biogas feedstock.

In some embodiments in which the biogas feedstock contains $H_2S$, step (b) may utilize absorption of the $H_2S$ into an absorption media (e.g., amines) to remove at least some of the $H_2S$ from the biogas feedstock.

In some embodiments, step (b) utilizes drying to remove at least some water from the biogas feedstock. This step may be omitted, for example, when the biogas is being fed to a SMR unit, in some embodiments.

The methane-to-syngas unit may be selected from the group consisting of a steam reforming reactor, an autothermal reforming reactor, a partial-oxidation reactor, and combinations thereof.

In some embodiments, in step (c), a pipeline natural gas stream is co-fed, along with the renewable natural gas stream, to the methane-to-syngas unit. Various fractions of renewable natural gas may be fed to the methane-to-syngas unit. In various embodiments, the percentage of renewable natural gas fed, relative to total natural gas, may be about, at least about, or at most about 1%, 2%, 5%, 10%, 15%, 20%, 25%, 30%, 35%, 40%, 45%, 50%, 55%, 60%, 65%, 70%, 75%, 80%, 85%, 90%, 95%, 99%, or 100%, including all intervening ranges.

It should also be noted that in step (c), it is possible to combine the renewable natural gas with another source of natural gas that is not necessarily from a pipeline or even pipeline-quality gas. For example, renewable natural gas may be combined with a refinery off-gas, or with a methane co-product of a chemical plant, for example.

Step (d) is performed in a syngas purification unit, which may comprise one or more individual unit operations. Step (d) may utilize an amine-based unit, a cryogenic unit, a membrane-separation unit, a pressure-swing adsorption unit, or a combination thereof. When step (d) utilizes multiple units, those multiple units are all contained within the syngas purification unit, in series, in parallel, or a combination thereof. In some embodiments, an amine-based unit is followed by a membrane unit. In other embodiments, a membrane unit is followed by an amine-based unit.

Amine-based units are known for removing $CO_2$ and $H_2S$ from gas streams. In such systems, the amine functions as a solvent to dissolve $CO_2$, which is later removed by adjusting conditions such as temperature. Any amine may be utilized as the solvent, such as diethanolamine (DEA), monoethanolamine (MEA), methyldiethanolamine (MDEA), diisopropanolamine (DIPA), or aminoethoxyethanol (DGA).

Cryogenic separation (or cryogenic distillation) may be used for the separation of $CH_4$, $CO_2$, $N_2$ and/or other components, from a syngas stream. Components of the syngas are separated using differences in their boiling points. The syngas may be pretreated to remove any impurities that would freeze at cryogenic temperatures, primarily water and carbon dioxide, and methane at cold enough temperatures.

In certain embodiments, step (d) employs a combination of an amine-based unit (referred to also as an amine system) and a cryogenic unit (referred to also as a cold box), in sequential unit operations to collectively remove $CO_2$, $CH_4$, $N_2$, and optionally $H_2$. It is important, in these embodiments, that the amine system is upstream of the cold box so that high amounts of $CO_2$ do not enter the cold box and potentially cause $CO_2$ freezing and plugging (a problem known as $CO_2$ freeze-out). In exemplary embodiments, a cryogenic separation unit is operated at a cold-box temperature of about −173° C. and a cold-box pressure of about 50 bar. At a pressure of 50 bar, methane can be separated at approximately −100° C., and nitrogen can be separated at approximately −150° C., for example.

Membrane-separation units utilize one or more membranes which enable separation via permeability differences of syngas components. Membranes may be fabricated from polymers, ceramics, and/or zeolites, for example. A multi-stage membrane design may be utilized to separate multiple components, such as $CH_4$, $CO_2$, and $N_2$ out of a $H_2/CO$ stream.

Pressure-swing adsorption (PSA) may be utilized in step (d). Pressure-swing adsorption processes are commonly utilized for the production of high-purity hydrogen. Pressure-swing adsorption separates gas species from a mixture of gases under pressure according to differences in species affinities for an adsorbent material. Specific adsorbent materials (e.g., zeolites, activated carbon, silica gel, etc.) are used as a trap, preferentially adsorbing the target gas species at high pressure. The process then swings to low pressure to desorb the adsorbed species. A PSA unit is desirable when a $H_2$-rich stream is desired syngas purification unit. Preferably, the pressure-swing adsorption unit (when present) is downstream of both the amine-based unit and the cryogenic unit.

In some embodiments, the $CO_2$-rich stream is compressed and used in enhanced oil recovery. In these or other embodiments, the $CO_2$-rich stream is sequestered in a geological formation. When the $CO_2$-rich stream is geologically sequestered, the environmental footprint is improved because there is a net reduction in greenhouse gas potential due to reduced $CO_2$ in the atmosphere. Enhanced oil recovery or sequestration into a geological formation removes a quantity of $CO_2$ from the atmosphere. Exemplary geological formations include underground caverns or geological storage horizons, where the $CO_2$ gas can be permanently stored. In some embodiments, underground caverns or geological storage horizons are contained in active or abandoned oil or natural gas fields. In certain embodiments, the $CO_2$ gas is injected unto an active oil or natural gas field and serves to increase production of oil or natural gas, where the $CO_2$ gas substantially remains sequestered in that oil or natural gas field during and after production. The separated $CO_2$ may be use in other ways, such as dry ice production or wastewater treatment. In certain embodiments, the $CO_2$ is further purified and sold for applications that require relatively high $CO_2$ purity, such as food-grade carbon dioxide or medical-grade dry ice, for example.

In some embodiments, in step (d), at least some of the $H_2$ is separated and recovered from the first syngas stream, into a hydrogen-rich stream. At least some of this $H_2$ may be used as fuel within the process, such as to heat the methane-to-syngas unit, especially when the methane-to-syngas unit is net-endothermic (e.g., in a steam-reforming reactor). Alternatively, or additionally, at least some of the $H_2$ is recovered as a motor fuel. Alternatively, or additionally, at least some of the $H_2$ is recovered and utilized in an oil and gas refinery, which lowers the carbon intensity of gasoline, diesel fuel, jet fuel, or other refinery products.

In some embodiments, in step (d), a methane-rich stream is separated from the first syngas stream. The methane-rich stream may be recycled to the methane-to-syngas unit. Alternatively, or additionally, the methane-rich stream may be combusted to provide heat to the methane-to-syngas unit. The methane-rich stream may be utilized as a fuel for a boiler or process heater. Alternatively, or additionally, the $CH_4$-rich stream may be utilized as a fuel for the methane-to-syngas unit, especially when the methane-to-syngas unit is net-endothermic (e.g., in a steam-reforming reactor).

In some embodiments, step (d) generates a $N_2$ stream that may be released to the atmosphere. In principle, the $N_2$ may be recovered and sold. The $N_2$ may be utilized in the Haber process for ammonia synthesis by reacting the $N_2$ with $H_2$ (e.g., the $H_2$-rich stream) to produce $NH_3$.

In some embodiments, in step (d), nitrogen is separated from the first syngas stream. The nitrogen may be purged from the process and released to the atmosphere or recovered for other uses, such as production of a liquid nitrogen co-product. The $N_2$ may be utilized in the Haber process for ammonia synthesis by reacting the $N_2$ with $H_2$ (e.g., the $H_2$-rich stream) to produce $NH_3$.

In the mixed-alcohol reactor, $H_2$ and CO are heated and passed over an alcohol synthesis catalyst such that at least a portion of the $H_2$ and CO are converted to $C_1$-$C_{10}$ (e.g., $C_1$-$C_5$) mixed alcohols. Co-products produced in the mixed-alcohol reactor typically include small quantities of water, carbon dioxide, and methane. The mixed alcohols are separated from the gas stream and are further purified, such as via sulfur removal, water removal (dehydration), and/or distillation. The separated gas stream may be recycled within the process.

Mixed alcohols may be synthesized in step (e) by passing the clean syngas stream over a potassium-promoted CoS—$MoS_2$ catalyst at about 300° C. and about 100 bar (as merely exemplary conditions for catalysis). See U.S. Pat. Nos. 4,752,622 and 4,882,360, which are hereby incorporated by reference. Processes and catalysts for making mixed alcohols are described in U.S. Pat. Nos. 8,921,431 and 9,290,425, which are hereby incorporated by reference.

In step (e), the alcohol-synthesis catalyst may be a metal sulfide catalyst, for example. The metal sulfide catalyst may be a catalyst comprising crystalline molybdenum sulfide, crystalline cobalt sulfide, and vanadium sulfide. The metal sulfide catalyst may be established in situ in the reactor by sulfiding a metal precursor, disposed within the reactor using a sulfur-containing agent to generate the metal sulfide catalyst.

In step (e), the reactor is pressurized and the syngas is passed over the alcohol-synthesis catalyst. The alcohol-synthesis catalyst and the syngas are heated and mixed alcohols are produced. The mixed-alcohol reaction subsystem may be designed and operated as described in U.S. Pat. No. 9,290,425, for example. The distribution of alcohols may be, for example, 17-31 wt % by weight methanol, 39-49 wt % ethanol, 19-29 wt % propanol, 4-12 wt % butanol, 0.1-5 wt % pentanol, and 0-10 wt % hexanol, heptanol, octanol, nonanol, decanol, ethers, esters, and hydrocarbons (inclusive of all isomers for any of these components).

In some embodiments, step (f) is conducted to produce a mixed-alcohol product. Step (f) may include one or more of sulfur removal, dehydration (water removal), and distillation, to generate a purified mixed-alcohol stream. In some embodiments, a reactor off-gas (from the mixed-alcohol reactor) is recycled to step (d), i.e., fed to the syngas purification unit. Optionally, the reactor off-gas is treated in a $H_2S$ removal unit prior to recycling to step (d).

The mixed-alcohol product may be blended with a hydrocarbon fuel selected from gasoline, diesel fuel, or jet fuel, to produce a blended fuel. Preferably, the blended fuel has a lower carbon intensity than the hydrocarbon fuel, due to the low carbon intensity associated with the mixed-alcohol product.

A "carbon intensity" (or "CI") of a fuel in this specification means the amount by weight of carbon dioxide, and greenhouse-gas equivalents of carbon dioxide, emitted per unit of energy contained in the fuel under consideration. The typical units of carbon intensity are grams carbon dioxide equivalent per megajoules of energy, or g $CO_2e$/MJ.

A greenhouse gas (or "GHG") is any gas in the atmosphere which absorbs and re-emits heat, and thereby keeps the planet's atmosphere warmer than it otherwise would be. The main GHGs in the Earth's atmosphere are water vapor, carbon dioxide, methane, nitrous oxide, and ozone. GHGs occur naturally in the Earth's atmosphere, but human activities, such as the burning of fossil fuels, are increasing the atmospheric levels of GHGs, causing at least some amount of global warming. Burning of fossil fuels is well-known to generate massive quantities of $CO_2$. By convention, the global-warming potential of $CO_2$ is defined to be 1. The global-warming potential of $CH_4$ is about 25, i.e., methane is 25× more potent than $CO_2$ as a greenhouse gas. See "IPCC Fourth Assessment Report: Climate Change 2007", Intergovernmental Panel on Climate Change, Cambridge University Press, Cambridge (2007), which is hereby incorporated by reference herein.

In order to calculate the carbon intensity of a mixed-alcohol product or a blended fuel as disclosed herein, the carbon intensities of the starting biogas need to be estimated, as do the carbon intensities associated with the upgrading of biomass to RNG, the conversion of RNG to syngas, the conversion of syngas to mixed alcohols, and the blending of mixed alcohols with hydrocarbons. One skilled in the art of chemical engineering is able to make these calculations. An important factor is the source of biogas. For example, animal biogas and landfill gas are normally released to the atmosphere which is problematic due to the global-warming potential of 25 for $CH_4$. By instead capturing and converting that $CH_4$, the carbon intensity is greatly decreased. Anaerobic digestion of lignocellulosic biomass may be treated differently because the starting biomass feedstock would not necessarily have biodegraded to methane. Life-cycle analysis may be employed to determine the carbon intensity associated with the starting biogas.

The carbon intensity of a commercial fuel is a very important parameter in the market today. The carbon intensity of gasoline meeting current California Air Resources Board (CARB) standard is 95.9 g $CO_2$e/MJ. The average carbon intensity of ethanol, according to *Ethanol Producers Magazine*, is about 68.6 $CO_2$e/MJ. The U.S. federal RFS2 and California LCFS benchmark gasoline carbon intensity is 93.25 $CO_2$e/MJ.

The carbon intensity of ordinary pipeline fossil natural gas is about 80.6 g $CO_2$e/MJ. By contrast, the carbon intensity of landfill gas can be about neutral (0), or about 50 to about −50 g $CO_2$e/MJ, while the carbon intensity of diary gas can be highly negative, such as about −250 to about −300 g $CO_2$e/MJ owing to the high $CH_4$ content and default release to the environment. When a mix of different sources of biogas—or a mix of biogas and pipeline natural gas—are utilized to produce mixed alcohols, the carbon intensity of the mixed-alcohol product will vary accordingly.

The carbon intensity of the mixed-alcohol product disclosed herein, in various embodiments, is about, or at most about, 50, 25, 0, −25, −50, −75, −100, −125, −150, −175, −200, −225, or −250 g $CO_2$e/MJ. In preferred embodiments, the mixed-alcohol product has a carbon intensity at least as low as −100 g $CO_2$e/MJ, and more preferably at least as low as −200 g $CO_2$e/MJ. The carbon intensity of the mixed alcohols can be negative when there is a negative carbon intensity of the starting biogas, as well as due to an energy-efficient conversion process.

When a blended fuel is created from mixed alcohols plus a hydrocarbon fuel, the carbon intensity of the blended fuel is based on the volume-weighted carbon intensities of each component. Thus for blended fuels with for example 5-15 vol % mixed alcohols in gasoline, there will be a reduction of carbon intensity compared to gasoline, while for higher blend levels such as 15-85 vol %, the reduction of carbon intensity is more drastic.

In some embodiments, the blended fuel has at least 10% lower carbon intensity than the hydrocarbon fuel. In preferred embodiments, the blended fuel has at least 20% lower carbon intensity than the hydrocarbon fuel. In even more-preferred embodiments, the blended fuel has at least 30% (such as about 33%) lower carbon intensity than the hydrocarbon fuel. These carbon-intensity reductions are typical when the blended fuel contains about 10 vol % mixed alcohols (as provided herein) and about 90 vol % convention fuel. When the blended fuel contains higher quantities of mixed alcohols, such as up to about 85 vol %, the carbon intensity may be at least 40%, 50%, 60%, 70%, 80%, 90%, 100%, 110%, 120%, 130%, 140%, or 150% lower than the carbon intensity than the hydrocarbon fuel. Values greater than 100% reduction are possible when the carbon intensity of the mixed alcohols is negative, such that the carbon intensity of the blended fuel drops below zero with enough mixed alcohols present.

Other variations provide a process for producing mixed alcohols, the process comprising:
 (a) obtaining a biogas feedstock;
 (b) purifying the biogas feedstock to generate a renewable natural gas stream comprising methane;
 (c) introducing the renewable natural gas stream to a pipeline, wherein the renewable natural gas stream is co-mingled with other natural gas contained within the pipeline;
 (d) withdrawing a stream of natural gas from the pipeline;
 (e) introducing the stream of natural gas into a methane-to-syngas unit operated at effective conditions to convert the methane to a first syngas stream containing at least $H_2$, CO, and $CO_2$;
 (f) purifying the first syngas stream, including separating the $CO_2$ from the first syngas stream, and optionally separating some of the $H_2$ from the first syngas stream, thereby generating a clean syngas stream;
 (g) introducing the clean syngas stream into a mixed-alcohol reactor operated at effective alcohol synthesis conditions and in the presence of an alcohol-synthesis catalyst, thereby generating mixed alcohols and a reactor off-gas; and
 (h) optionally purifying the mixed alcohols to generate a mixed-alcohol product.

Figure 2:
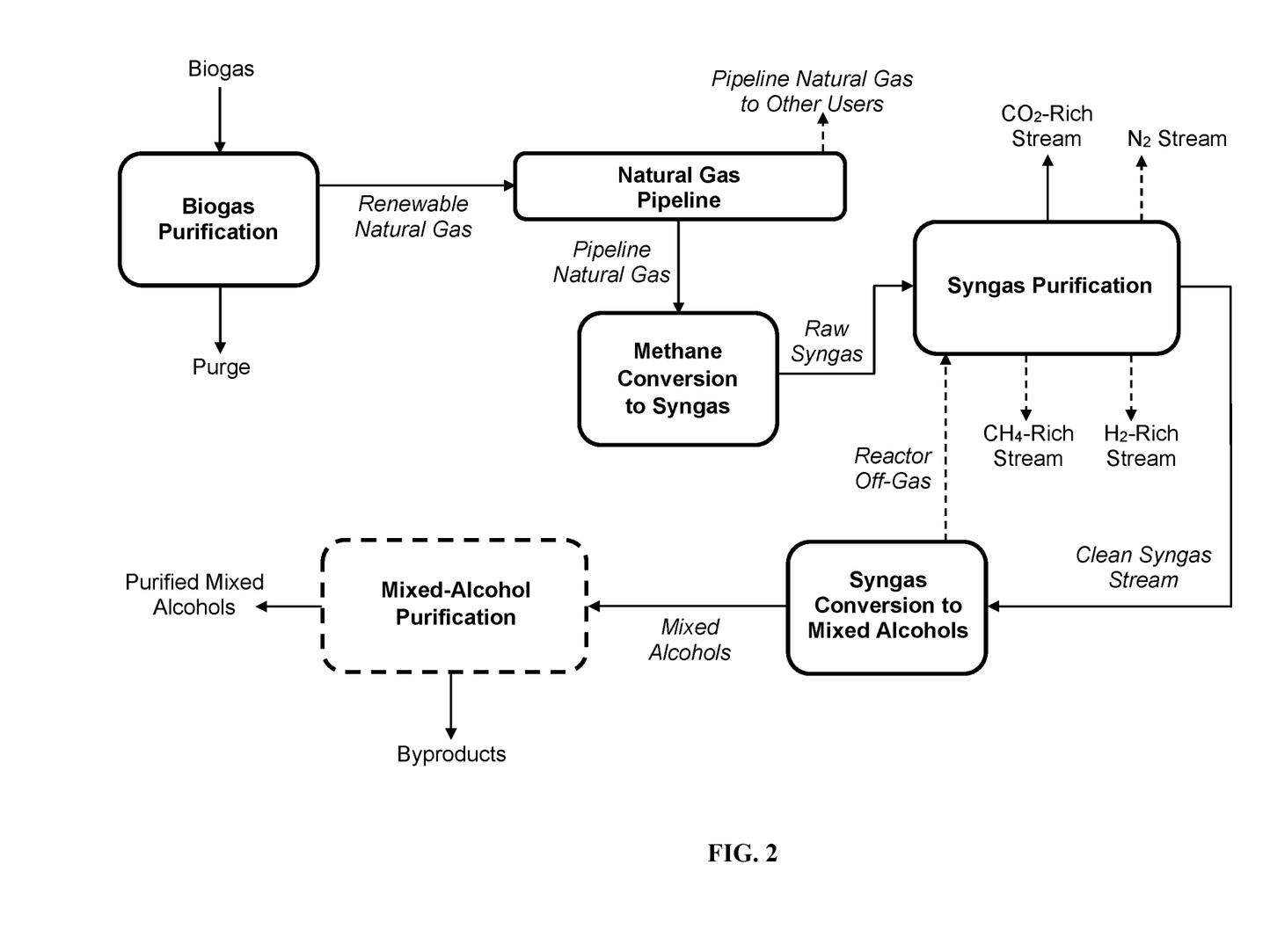
FIG. 2 is an exemplary block-flow diagram according to some embodiments for mixed-alcohol production from biogas.

FIG. 2 is an exemplary block-flow diagram according to some embodiments for mixed-alcohol production from biogas, employing co-mingling of biogas with other natural gas contained within a pipeline. Note that not all process boxes in FIG. 2 are required in all embodiments. Dotted boxes and lines denote optional units and streams, respectively.

The biogas feedstock may be obtained from a source selected from the group consisting of a landfill, an industrial compost facility, an anaerobic digestor, and combinations thereof. An anaerobic digestor may be configured for anaerobic digestion of animal waste, for example.

Step (b) is typically included in the process to purify the biogas, since the biogas must be high quality before injection and co-mingling into a natural gas pipeline.

Step (b) may utilize water scrubbing, chemical scrubbing, or a combination thereof to remove at least some carbon dioxide from the biogas feedstock. In some embodiments, step (b) utilizes a membrane to remove at least some carbon dioxide from the biogas feedstock.

When the biogas feedstock contains $H_2S$, step (b) may utilize absorption of the $H_2S$ into an absorption media to remove at least some of the $H_2S$ from the biogas feedstock.

In some embodiments, step (b) utilizes drying to remove at least some water from the biogas feedstock.

In some embodiments, step (c) generates a renewable natural gas credit that applies to the mixed alcohols produced in step (g). When step (h) is conducted, step (c) may generate a renewable natural gas credit that applies to the mixed-alcohol product produced in step (h). The renewable natural gas credit may be provided by the operator of the natural gas pipeline, a government agency that regulates the natural gas pipeline, a non-governmental organization (NGO) that advocates for renewal fuels, and/or another entity. There may be renewable natural gas credits associated with the process, the product, or both of these.

The methane-to-syngas unit may be selected from the group consisting of a steam reforming reactor, an autothermal reforming reactor, a partial-oxidation reactor, and combinations thereof.

In some processes, in step (e), a pipeline natural gas stream is co-fed, along with the renewable natural gas stream (withdrawn in step (d)), to the methane-to-syngas unit. Typically, the pipeline natural gas stream is distinct from the initial natural gas that is co-mingled with the renewable natural gas stream in step (c). The pipeline natural gas stream co-fed in step (e) may itself contain some renewable natural gas.

In step (c), various fractions of renewable natural gas may be co-mingled with pipeline natural gas. When renewable natural gas is injected into a pipeline at an injection point, there will be a nominal volumetric flow rate of natural gas within the pipeline at that point. The renewable natural gas is injected with its own flow rate, which may be from about 0.1% to 100% of the nominal pipeline flow rate, for example. The actual concentration of renewable natural gas within the pipeline would depend on not only injection rate but also whether the injection is continuous or intermittent. For at least these reasons, it is difficult for a user of pipeline natural gas (such as the entity carrying out step (d) above) to ascertain whether the natural gas being purchased is renewable or non-renewable, unless isotope analysis is carried out. Infrastructure limitations may be addressed by regulatory mechanisms, such as renewable credits that are earned when renewable natural gas is added to a pipeline. Such renewable credits may be purchased by a gas user who seeks to lower the effective carbon intensity of the user's product derived from the purchased gas.

In step (e), various fractions of renewable natural gas may be fed to the methane-to-syngas unit. In various embodiments, the percentage of renewable natural gas fed, relative to total natural gas, may be about, at least about, or at most about 1%, 2%, 5%, 10%, 15%, 20%, 25%, 30%, 35%, 40%, 45%, 50%, 55%, 60%, 65%, 70%, 75%, 80%, 85%, 90%, 95%, 99%, or 100%, including all intervening ranges.

It should also be noted that in step (e), it is possible to combine the renewable natural gas with another source of natural gas that is not necessarily from a pipeline or even pipeline-quality gas. For example, renewable natural gas may be combined with a refinery off-gas, or with a methane co-product of a chemical plant, for example.

In some embodiments, in step (f), at least some of the $H_2$ is separated and recovered from the first syngas stream. At least some of this $H_2$ may be used as fuel within the process. Alternatively, or additionally, at least some of the $H_2$ is recovered as a motor fuel. Alternatively, or additionally, at least some of the $H_2$ is recovered and utilized in an oil and gas refinery.

In some embodiments, step (f) utilizes an amine-based system, a cryogenic system, a membrane-separation system, a pressure-swing adsorption unit, or a combination thereof.

In some embodiments, the $CO_2$ separated in step (f) is recovered and sequestered in a geological formation. Alternatively, or additionally, the $CO_2$ separated in step (f) may be recovered and utilized in enhanced oil recovery.

In some embodiments, in step (f), nitrogen is separated from the first syngas stream. The nitrogen may be purged from the process and released from the atmosphere or recovered for other uses, such as production of a liquid nitrogen co-product.

In some embodiments, in step (f), a methane-rich stream is separated from the first syngas stream. The methane-rich stream may be recycled to the methane-to-syngas unit. Alternatively, or additionally, the methane-rich stream may be combusted to provide heat to the methane-to-syngas unit.

In the mixed-alcohol reactor, $H_2$ and CO are heated and passed over an alcohol synthesis catalyst such that at least a portion of the $H_2$ and CO are converted to $C_1$-$C_{10}$ (e.g., $C_1$-$C_5$) mixed alcohols. Co-products produced in the mixed-alcohol reactor typically include small quantities of water, carbon dioxide, and methane. The mixed alcohols are separated from the gas stream and are further purified, such as via sulfur removal, water removal (dehydration), and/or distillation. The separated gas stream may be recycled within the process.

Mixed alcohols may be synthesized in step (g) by passing the clean syngas stream over a potassium-promoted CoS—$MoS_2$ catalyst at about 300° C. and about 100 bar (as merely exemplary conditions for catalysis). See U.S. Pat. Nos. 4,752,622 and 4,882,360, which are hereby incorporated by reference. Processes and catalysts for making mixed alcohols are described in U.S. Pat. Nos. 8,921,431 and 9,290,425, which are hereby incorporated by reference.

In step (g), the alcohol-synthesis catalyst may be a metal sulfide catalyst, for example. The metal sulfide catalyst may be a catalyst comprising crystalline molybdenum sulfide, crystalline cobalt sulfide, and vanadium sulfide. The metal sulfide catalyst may be established in situ in the reactor by sulfiding a metal precursor, disposed within the reactor using a sulfur-containing agent to generate the metal sulfide catalyst.

In step (g), the reactor is pressurized and the syngas is passed over the alcohol-synthesis catalyst. The alcohol-synthesis catalyst and the syngas are heated and mixed alcohols are produced. The mixed-alcohol reaction subsystem may be designed and operated as described in U.S. Pat. No. 9,290,425, for example. The distribution of alcohols may be, for example, 17-31 wt % by weight methanol, 39-49 wt % ethanol, 19-29 wt % propanol, 4-12 wt % butanol, 0.1-5 wt % pentanol, and 0-10 wt % hexanol, heptanol, octanol, nonanol, decanol, ethers, esters, and hydrocarbons (inclusive of all isomers for any of these components).

In some embodiments, step (h) is conducted to produce a mixed-alcohol product. Step (h) may include one or more of sulfur removal, dehydration (water removal), and distillation, to generate a purified mixed-alcohol stream. In some embodiments, a reactor off-gas (from the mixed-alcohol reactor) is recycled to step (f), i.e., fed to the syngas purification unit. Optionally, the reactor off-gas is treated in a $H_2S$ removal unit prior to recycling to step (f).

The mixed-alcohol product may be blended with a hydrocarbon fuel selected from gasoline, diesel fuel, or jet fuel, to produce a blended fuel. Preferably, the blended fuel has a lower carbon intensity than the hydrocarbon fuel, due to the low carbon intensity associated with the mixed-alcohol product. In some embodiments, the blended fuel has at least 10% lower carbon intensity than the hydrocarbon fuel. In preferred embodiments, the blended fuel has at least 20% lower carbon intensity than the hydrocarbon fuel. In even more-preferred embodiments, the blended fuel has at least 30% lower carbon intensity than the hydrocarbon fuel.

Significant environmental advantages result from producing biogas from landfills, anaerobic digestion of animal waste, or other sources, and utilizing clean-up technologies to produce renewable natural gas or otherwise acquiring (e.g., purchasing) renewable natural gas for the production of syngas, and then optionally converting that syngas to mixed alcohols. By using renewable natural gas or a blend of renewable natural gas and fossil natural gas, a mixed-alcohol fuel additive enables the production of gasoline blended fuels with significantly lower carbon intensity compared to conventional gasoline.

A blended fuel that incorporates mixed alcohols as disclosed herein can be shown to contain renewable carbon (i.e., carbon that is derived from renewable sources such as biomass), rather than non-renewable fossil sources). This can be shown from a measurement of the $^{14}C/^{12}C$ isotopic ratio of the carbon in a sample of the blended fuel or the mixed-alcohol product itself. When a fuel is burned for energy, $CO_2$ returns to the environment to be taken up again by growing biomass via photosynthesis. In this way, net $CO_2$ emissions are significantly reduced.

Additionally, a byproduct stream of renewable hydrogen may be produced and utilized directly as a motor fuel or used within a hydrocarbon refinery to reduce the environmental impact of gasoline or other hydrocarbon products. For example, the renewable hydrogen provided herein may be utilized in a standard refinery, or in a biorefinery, that requires an on-site source of hydrogen. As just a few examples, a typical refinery uses hydrogen for hydrotreating, hydrodesulfurization, and hydrogenation. Renewable hydrogen may be recognized in the market in various ways, such as through renewable-energy standards, renewable-energy credits, renewable identification numbers, and the like. As just one example, an oil refinery utilizing renewable hydrogen in producing gasoline may be able to receive renewable-energy credit for such $H_2$ content.

As noted above, measuring the $^{14}C/^{12}C$ isotopic ratio of carbon is a proven technique. A similar concept may be applied to hydrogen, in which the $^2H/^1H$ isotopic ratio is measured ($^2H$ is also known as deuterium, D). Fossil sources tend to be depleted in deuterium compared to biomass. See Schiegl et al., "Deuterium content of organic matter", *Earth and Planetary Science Letters*, Volume 7, Issue 4, 1970, Pages 307-313; and Hayes, "Fractionation of the Isotopes of Carbon and Hydrogen in Biosynthetic Processes", Mineralogical Society of America, National Meeting of the Geological Society of America, Boston, Ma., 2001, which are hereby incorporated by reference herein.

Some variations provide a process for producing low-carbon-intensity syngas, the process comprising:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream; and (e) recovering the clean syngas stream as a low-carbon-intensity syngas.

Other variations provide a process for producing low-carbon-intensity syngas, the process comprising:

(a) obtaining a biogas feedstock;

(b) purifying the biogas feedstock to generate a renewable natural gas stream comprising methane;

(c) introducing the renewable natural gas stream to a pipeline, wherein the renewable natural gas stream is co-mingled with other natural gas contained within the pipeline;

(d) withdrawing a stream of natural gas from the pipeline;

(e) introducing the stream of natural gas into a methane-to-syngas unit operated at effective conditions to convert the methane to a first syngas stream containing at least $H_2$, CO, and $CO_2$;

(f) purifying the first syngas stream, including separating the $CO_2$ from the first syngas stream, and optionally separating some of the $H_2$ from the first syngas stream, thereby generating a clean syngas stream; and (g) recovering the clean syngas stream as a low-carbon-intensity syngas.

The low-carbon-intensity syngas may have at least 5%, 10%, 20%, 30%, 40%, 50%, 60%, 70%, 80%, 90%, or 100% lower carbon intensity compared to otherwise-equivalent syngas produced from natural gas that does not include any RNG. The carbon intensity of the low-carbon-intensity syngas may be about, or at most about, 50, 25, 0, −25, −50, −100, −150, −200, −250, −300, −350, −400, −450, −500, −550, −600, −650, or −700 g $CO_2e/MJ$, including all intervening ranges.

A system is also provided, wherein the system is configured to carry out any of the disclosed processes.

For example, a system may be configured to carry out the steps of:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream;

(e) introducing the clean syngas stream into a mixed-alcohol reactor operated at effective alcohol synthesis conditions and in the presence of an alcohol-synthesis catalyst, thereby generating mixed alcohols and a reactor off-gas; and (f) optionally purifying the mixed alcohols to generate a mixed-alcohol product.

The present invention provides a system for producing mixed alcohols, the system comprising:

a biogas purification unit configured to purify a biogas feedstock to generate a renewable natural gas stream comprising methane;

a methane-to-syngas unit operated at effective conditions to convert the methane to a first syngas stream containing at least $H_2$, CO, and $CO_2$;

a syngas purification unit configured to purify the first syngas stream, including separating the $CO_2$ from the first syngas stream, and optionally separating some of the $H_2$ from the first syngas stream, thereby generating a clean syngas stream;

a mixed-alcohol reactor configured to convert the clean syngas stream to mixed alcohols when operated at effective alcohol synthesis conditions and in the presence of an alcohol-synthesis catalyst, thereby generating mixed alcohols and a reactor off-gas; and optionally, a mixed-alcohols purification unit configured to purify the mixed alcohols to generate a mixed-alcohol product.

A system that utilizes natural gas co-mingling may be configured to carry out the steps of:

(a) obtaining a biogas feedstock;

(b) purifying the biogas feedstock to generate a renewable natural gas stream comprising methane;

(c) introducing the renewable natural gas stream to a pipeline, wherein the renewable natural gas stream is co-mingled with other natural gas contained within the pipeline;

(d) withdrawing a stream of natural gas from the pipeline;

(e) introducing the stream of natural gas into a methane-to-syngas unit operated at effective conditions to convert the methane to a first syngas stream containing at least $H_2$, CO, and $CO_2$;

(f) purifying the first syngas stream, including separating the $CO_2$ from the first syngas stream, and optionally separating some of the $H_2$ from the first syngas stream, thereby generating a clean syngas stream;

(g) introducing the clean syngas stream into a mixed-alcohol reactor operated at effective alcohol synthesis conditions and in the presence of an alcohol-synthesis catalyst, thereby generating mixed alcohols and a reactor off-gas; and (h) optionally purifying the mixed alcohols to generate a mixed-alcohol product.

The present invention provides a system for producing mixed alcohols, the system comprising:

a biogas purification unit configured to purify a biogas feedstock to generate a renewable natural gas stream comprising methane;

an input connection to a natural gas pipeline, configured to introduce the renewable natural gas stream to the pipeline, wherein the renewable natural gas stream is co-mingled with other natural gas contained within the pipeline;

an output connection from the natural gas pipeline;

a methane-to-syngas unit operated at effective conditions to convert natural gas, from the natural gas pipeline, to a first syngas stream containing at least $H_2$, CO, and $CO_2$;

a syngas purification unit configured to purify the first syngas stream, including separating the $CO_2$ from the first syngas stream, and optionally separating some of the $H_2$ from the first syngas stream, thereby generating a clean syngas stream;

a mixed-alcohol reactor configured to convert the clean syngas stream to mixed alcohols when operated at effective alcohol synthesis conditions and in the presence of an alcohol-synthesis catalyst, thereby generating mixed alcohols and a reactor off-gas; and optionally, a mixed-alcohols purification unit configured to purify the mixed alcohols to generate a mixed-alcohol product.

Also provided is a mixed-alcohol composition produced by any of the disclosed processes. The mixed-alcohol composition may be as described in U.S. Pat. Nos. 8,921,431 or 9,290,425, or another composition.

For example, some embodiments provide a mixed-alcohol product produced by a process comprising:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream;

(e) introducing the clean syngas stream into a mixed-alcohol reactor operated at effective alcohol synthesis conditions and in the presence of an alcohol-synthesis catalyst, thereby generating mixed alcohols and a reactor off-gas; and (f) optionally purifying the mixed alcohols to generate a mixed-alcohol product.

Some embodiments provide a mixed-alcohol product utilizing natural gas co-mingling, produced by a process comprising:

(a) obtaining a biogas feedstock;

(b) purifying the biogas feedstock to generate a renewable natural gas stream comprising methane;

(c) introducing the renewable natural gas stream to a pipeline, wherein the renewable natural gas stream is co-mingled with other natural gas contained within the pipeline;

(d) withdrawing a stream of natural gas from the pipeline;

(e) introducing the stream of natural gas into a methane-to-syngas unit operated at effective conditions to convert the methane to a first syngas stream containing at least $H_2$, CO, and $CO_2$;

(f) purifying the first syngas stream, including separating the $CO_2$ from the first syngas stream, and optionally separating some of the $H_2$ from the first syngas stream, thereby generating a clean syngas stream;

(g) introducing the clean syngas stream into a mixed-alcohol reactor operated at effective alcohol synthesis conditions and in the presence of an alcohol-synthesis catalyst, thereby generating mixed alcohols and a reactor off-gas; and (h) optionally purifying the mixed alcohols to generate a mixed-alcohol product.

Still other variations provide a low-carbon-intensity syngas produced by a process comprising:

(a) obtaining a biogas feedstock;

(b) purifying the biogas feedstock to generate a renewable natural gas stream comprising methane;

(c) introducing the renewable natural gas stream into a methane-to-syngas unit operated at effective conditions to convert the methane to a first syngas stream containing at least $H_2$, CO, and $CO_2$;

(d) purifying the first syngas stream, including separating the $CO_2$ from the first syngas stream, and optionally separating some of the $H_2$ from the first syngas stream, thereby generating a clean syngas stream; and (e) recovering the clean syngas stream as a low-carbon-intensity syngas.

Still other variations, relating to natural gas co-mingling, provide a low-carbon-intensity syngas produced by a process comprising:

(a) obtaining a biogas feedstock;

(b) purifying the biogas feedstock to generate a renewable natural gas stream comprising methane;

(c) introducing the renewable natural gas stream to a pipeline, wherein the renewable natural gas stream is co-mingled with other natural gas contained within the pipeline;

(d) withdrawing a stream of natural gas from the pipeline;

(e) introducing the stream of natural gas into a methane-to-syngas unit operated at effective conditions to convert the methane to a first syngas stream containing at least $H_2$, CO, and $CO_2$;

(f) purifying the first syngas stream, including separating the $CO_2$ from the first syngas stream, and optionally separating some of the $H_2$ from the first syngas stream, thereby generating a clean syngas stream; and (g) recovering the clean syngas stream as a low-carbon-intensity syngas.

As will be appreciated by a skilled engineer, the processes and systems of the invention may employ various process sensors and control schemes to monitor and control gas pressures, temperatures, flow rates, and compositions throughout processing. Standard or customized gas pressure, temperature, and flow gauges may be employed. Gas composition may be monitored by withdrawing a gas sample and subjecting the gas sample to mass spectrometry, gas chromatography, or FTIR spectroscopy, for example. Gas composition may be measured, for example, according to ASTM D7833, D1945, D1946, or D3588, which test methods are incorporated by reference herein. Process adjustments may be made dynamically using measurements of gas pressures, temperatures, flow rates, and/or compositions, if deemed necessary or desirable, using well-known principles of process control (feedback, feedforward, proportional-integral-derivative logic, etc.).

As will also be appreciated by a skilled artisan, the processes and systems of the invention may utilize various process simulations, modeling, and engineering calculations, both in the initial design as well as during operation. Process calculations and simulations may be performed using process simulation software.

The present invention may be applied to a wide range of throughputs and product generation capacities, such as from about 1,000 liters/day to about 1,000,000 liters/day of mixed alcohols, or from about 10 MMSCFD to about 10,000 MMSCFD of a clean syngas product, for example.

The syngas produced as described according to the present invention may be utilized in a number of ways, beyond mixed alcohols. Syngas can be chemically converted into methane, olefins (such as ethylene), oxygenates (such as dimethyl ether), paraffins, linear or branched $C_5$-$C_{15}$ hydrocarbons, diesel fuel, gasoline, or waxes, such as by Fischer-Tropsch chemistry. Syngas can be converted into isobutane by isosynthesis. Syngas can be converted to aldehydes and alcohols by oxosynthesis. Syngas can be converted to methanol as an intermediate for making methanol derivatives including dimethyl ether, acetic acid, ethylene, propylene, or formaldehyde. Syngas can also be converted to energy using energy-conversion devices such as solid-oxide fuel cells, Stirling engines, micro-turbines, internal combustion engines, thermo-electric generators, scroll expanders, gas burners, or thermo-photovoltaic devices.

In addition to the mixed alcohols or clean syngas as primary product, there may be a number of co-products from the processes and systems of the invention. Co-products may include, but are not limited to, $CH_4$, $H_2$, CO, $CO_2$, $N_2$, $H_2O$, hydrocarbons, and electricity generated on-site, for example.

EXAMPLE

This example illustrates biogas utilization for mixed alcohol production, according to the principles of the invention described above. The flow rates and concentrations in this Example are merely exemplary and not intended to limit the invention as claimed.

This example is a process simulation carried out using Aspen Plus® software (Aspen Technology Inc., Bedford, Ma., USA). Using Aspen Plus, a process model is built and then the process is simulated using complex calculations involving unit operations, chemical reactions, thermodynamic properties, and so on, to predict performance of the designed process.

This Example utilizes a process flow starting with 16 MMSCFD (million standard cubic feet per day) of biogas that is 61 vol % $CH_4$, 36 vol % $CO_2$, 2 vol % $H_2O$, and 2 vol % $N_2$ (16 MMSCFD is about 5.3 standard $m^3$/s). The biogas is upgraded using amine scrubbing to 9.7 MMSCFD renewable natural gas that is 97 vol % $CH_4$, 1.5 vol % $CO_2$, and 1.5 vol % $N_2$. A steam methane reforming unit produces 63.8 MMSCFD of syngas that is 31.5 vol % $H_2$, 21 vol % CO, 10.3 vol % $CO_2$, 5.2 vol % $CH_4$, 1.1 vol % $N_2$, and 1.1 vol % $H_2O$.

The output of the steam methane reforming unit enters an amine system. The feed stream to the amine system is a combination of the steam methane reforming output and off-gas recycled from the downstream mixed-alcohol reactor (see below). The amine system is a conventional amine-separation unit. The specific amine solvent employed is methyldiethanolamine (MDEA). In an absorber column, $CO_2$ is absorbed into the MDEA to form a soluble carbonate salt. The absorber operates at 50° C. and 30 bar pressure. In a stripping column, the $CO_2$ is released by heating the carbonate salt at 90° C. and a pressure of about 1.5 bar. The amine system produces a purified gas (also referred to as sweet gas) with a flow rate of 149.6 MMSCFD and a composition that is 45.3 vol % $H_2$, 38.5 vol % CO, 8.3 vol % $CO_2$, 3.6 vol % $CH_4$, 2.6 vol % $N_2$, and 1.8 vol % $H_2O$.

In the amine system, concentrated (100 vol %) $CO_2$ is separated out. 12.3 MMSCFD $CO_2$ is produced for enhanced oil recovery, sequestration into a geological formation, dry ice production, wastewater treatment, or other uses. The $CO_2$ may be compressed to a suitable pressure for enhanced oil recovery or sequestration, such as about 50-100 bar. The high-purity $CO_2$ may be further purified and sold for applications that require relatively high $CO_2$ purity, such as to the food/beverage industry or use as medical-grade dry ice, for example.

The gas from the amine system is sent to a membrane unit. The membrane unit produces 134.9 MMSCFD of a membrane retentate gas that is 50.2 vol % $H_2$, 42.7 vol % CO, 0.1 vol % $CO_2$, 3.9 vol % $CH_4$, 2.8 vol % $N_2$, and 0.2 vol % $H_2O$. The membrane unit produces 13.7 MMSCFD of a membrane permeate gas that is 100 vol % $H_2$. This excess, high-purity $H_2$ may be sold, such as to an adjacent refinery for on-site hydrogen requirements. The hydrogen may be utilized in the steam methane reformer burners to displace natural gas or other fuels needing to be burned to generate the necessary energy for endothermic steam reforming. In other scenarios in which a different $H_2$/CO ratio is desired for the clean syngas, there may or may not be excess hydrogen available.

Another output of the membrane unit is a fuel gas stream at a flow rate of 8.9 MMCSFD, containing 60 vol % $CH_4$ and 40 vol % CO. The fuel gas stream has a high energy value when combusted. The heat of combustion may be utilized to drive the endothermic steam reforming in the steam methane reforming system. Optionally, because the fuel gas stream is mostly methane, this stream may be recycled to feed the steam methane reforming system.

From the membrane unit, 3.8 MMSCFD $N_2$ is released to the atmosphere. $N_2$ is not a greenhouse gas and is the majority of ordinary air. In principle, the $N_2$ may be recovered and sold. For example, the $N_2$ may be utilized in the Haber process for ammonia synthesis by reacting the $N_2$ with $H_2$ (e.g., the excess $H_2$ stream) to produce $NH_3$.

Note that the membrane unit may be replaced by a cold box (cryogenic separation unit), or there may be both a membrane unit and a cold box.

The clean syngas stream has a flow rate of 125.3 MMSCFD and is 54 vol % $H_2$ and 46 vol % CO. This clean syngas stream is fed to a syngas compressor, to raise the syngas pressure to about 100 bar. The compressed syngas is also preheated to a temperature of about 300° C. The compressed, preheated syngas is fed to a mixed-alcohol reactor.

The mixed-alcohol reactor is configured to carry out catalyzed mixed-alcohol synthesis to produce approximately 286,000 liters per day of high-value and environmentally friendly mixed alcohols. Mixed alcohols are synthesized by passing the cleaned syngas over a potassium-promoted $CoS$—$MoS_2$ catalyst at about 300° C. and about 100 bar. In the mixed-alcohol reactor, $H_2$ and CO are heated and passed over an alcohol synthesis catalyst to generate methanol, ethanol, propanol, butanol, pentanol, and small amounts of higher alcohols. The syngas conversion to mixed alcohols in the mixed-alcohol reactor is about 30%. The consumed syngas is 35.2 MMSCFD (17.5 MMSCFD CO and 17.8 MMSCFD $H_2$). Co-products produced in the mixed-alcohol reactor include small quantities of water, carbon dioxide, and methane.

Following mixed-alcohol synthesis, a mixed-alcohol stream is generated, as well as a reactor off-gas. The flow rate of the reactor off-gas is 85.8 MMSCFD, and its composition is 42.2 vol % $H_2$, 42.6 vol % CO, 6.9 vol % $CO_2$, 2.4 vol % $CH_4$, 3.7 vol % Na, and 2.3 vol % $H_2O$. The reactor off-gas is let-down in pressure and is fed to a $H_2S$ removal unit. The $H_2S$ removal unit utilizes adsorbent media, such as an iron-based scavenger, to selectively adsorb $H_2S$. Following $H_2S$ removal, the off-gas is recycled to the amine system as noted earlier. If the reactor off-gas does not contain much $H_2S$, the $H_2S$ removal unit may be omitted. The reactor off-gas may also be purged from the process and not internally recycled. Also, the $H_2S$ removal units is optional.

The raw mixed-alcohol stream is fed to a sulfur-removal unit. The sulfur-removal unit includes a sulfur absorbent such as an ion-exchange resin, activated carbon, alumina, aluminum silicate, or a combination thereof, to absorb or adsorb sulfur-containing compounds from the raw mixed-alcohol stream, forming a low-sulfur mixed-alcohol stream. The sulfur absorbent is regenerable using a heated, inert stripping gas for regenerating the sulfur absorbent beds. The stripping gas may be nitrogen, optionally including $N_2$ recycled from the cryogenic separation unit, and may be heated using electrical heating, for example. If the raw mixed-alcohol stream does not contain much sulfur, the sulfur-removal unit may be omitted.

The low-sulfur mixed-alcohol stream is fed to a dehydrator to remove water from the mixed alcohols. The dehydrator contains zeolite-based molecular-sieve membranes for water adsorption. Dehydration occurs prior to distillation.

The dehydrated, low-sulfur mixed-alcohol stream is fed to a distillation column to remove a majority of the impurities (primarily methanol), resulting in a mixed-alcohol product. This simulated process produces 286,000 liters per day of high-value and environmentally friendly mixed alcohols. The mixed-alcohol product may be referred to as OctaneX® mixed alcohols.

The clean syngas stream alternatively may be recovered and sold, rather than being converted to mixed alcohols. The clean syngas stream may ultimately be converted to a wide variety of final products.

In the simulated process, high-pressure steam is generating using excess heat from the mixed-alcohol reactor. The high-pressure steam is sent to a cogeneration unit in which the steam is superheated and then used in a turbine to generate electricity. About 9 MW/hr of power is generated for the entire process including process pumps, a vacuum pump used in the dehydration unit, and a heater used in the sulfur removal unit. The high-pressure steam cogeneration unit is optional.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing mixed alcohols, said process comprising:
   (a) obtaining a biogas feedstock;
   (b) purifying said biogas feedstock to generate a renewable natural gas stream comprising methane;
   (c) introducing said renewable natural gas stream into a methane-to-syngas unit operated at effective conditions to convert said methane to a first syngas stream containing at least $H_2$, CO, and $CO_2$;
   (d) purifying said first syngas stream, including separating said $CO_2$ from said first syngas stream, and optionally separating some of said $H_2$ from said first syngas stream, thereby generating a clean syngas stream;
   (e) introducing said clean syngas stream into a mixed-alcohol reactor operated at effective alcohol synthesis conditions and in the presence of an alcohol-synthesis catalyst, thereby generating mixed alcohols and a reactor off-gas;
   (f) purifying said mixed alcohols to generate a mixed-alcohol product; and
   (g) blending said mixed-alcohol product with a hydrocarbon fuel selected from gasoline, diesel fuel, or jet fuel, to produce a blended fuel, wherein said blended fuel has at least 10% lower carbon intensity than said hydrocarbon fuel.

2. The process of claim 1, wherein said biogas feedstock is obtained from a source selected from the group consisting of a landfill, an industrial compost facility, an anaerobic digestor, and combinations thereof.

3. The process of claim 1, wherein said anaerobic digestor is configured for anaerobic digestion of animal waste.

4. The process of claim 1, wherein step (b) utilizes water scrubbing, chemical scrubbing, or a combination thereof to remove at least some carbon dioxide from said biogas feedstock.

5. The process of claim 1, wherein step (b) utilizes a membrane to remove at least some carbon dioxide from said biogas feedstock.

6. The process of claim 1, wherein said biogas feedstock contains $H_2S$, and wherein step (b) utilizes absorption of said H₂S into an absorption media to remove at least some of said H$_2$S from said biogas feedstock.

7. The process of claim 1, wherein step (b) utilizes drying to remove at least some water from said biogas feedstock.

8. The process of claim 1, wherein said methane-to-syngas unit is selected from the group consisting of a steam reforming reactor, an autothermal reforming reactor, a partial-oxidation reactor, and combinations thereof.

9. The process of claim 1, wherein in step (c), a pipeline natural gas stream is co-fed, along with said renewable natural gas stream, to said methane-to-syngas unit.

10. The process of claim 1, wherein in step (d), at least some of said H$_2$ is separated and recovered from said first syngas stream.

11. The process of claim 1, wherein step (d) utilizes an amine-based system, a cryogenic system, a membrane-separation system, a pressure-swing adsorption unit, or a combination thereof.

12. The process of claim 1, wherein said CO$_2$ separated in step (d) is recovered and sequestered in a geological formation.

13. The process of claim 1, wherein said CO$_2$ separated in step (d) is recovered and utilized in enhanced oil recovery.

14. The process of claim 1, wherein in step (d), nitrogen is separated from said first syngas stream.

15. The process of claim 1, wherein in step (d), a methane-rich stream is separated from said first syngas stream.

16. The process of claim 1, wherein in step (e), said alcohol-synthesis catalyst is a metal sulfide catalyst.

17. The process of claim 1, wherein step (f) includes one or more of sulfur removal, dehydration, and distillation.

18. The process of claim 1, wherein said reactor off-gas is recycled to step (d), and wherein said reactor off-gas is optionally treated in a H$_2$S removal unit prior to recycling to step (d).

* * * * *